(12) United States Patent
Moriishi et al.

(10) Patent No.: US 8,580,759 B2
(45) Date of Patent: Nov. 12, 2013

(54) ANTI-HEPATITIS C VIRUS COMPOSITION

(75) Inventors: Kohji Moriishi, Osaka (JP); Yoshiharu Matsuura, Osaka (JP)

(73) Assignee: Osaka University, Osaka (JP)

( * ) Notice: Subject to any disclaimer, the term of this patent is extended or adjusted under 35 U.S.C. 154(b) by 63 days.

(21) Appl. No.: 13/060,474

(22) PCT Filed: Aug. 28, 2009

(86) PCT No.: PCT/JP2009/065072
§ 371 (c)(1),
(2), (4) Date: Mar. 18, 2011

(87) PCT Pub. No.: WO2010/024384
PCT Pub. Date: Mar. 4, 2010

(65) Prior Publication Data
US 2011/0166203 A1   Jul. 7, 2011

(30) Foreign Application Priority Data

Aug. 29, 2008 (JP) .................................. 2008-221980

(51) Int. Cl.
*C12N 15/113* (2010.01)
*C07H 21/04* (2006.01)
(52) U.S. Cl.
USPC ....................................... 514/44 A; 536/24.5
(58) Field of Classification Search
None
See application file for complete search history.

(56) References Cited

U.S. PATENT DOCUMENTS

| 2004/0106539 | A1 | 6/2004 | Schubert |
| 2007/0265194 | A1 | 11/2007 | Schubert |
| 2010/0297605 | A1* | 11/2010 | Matsuura et al. ............. 435/5 |

FOREIGN PATENT DOCUMENTS

| EP | 2098598 | 9/2009 |
| JP | 2004-510826 | 4/2004 |
| WO | 02/100333 | 12/2002 |
| WO | 2008/041665 | 4/2008 |
| WO | 2008/121442 | 10/2008 |

OTHER PUBLICATIONS

Abstract for WO 2008/121442, published Oct. 9, 2008, 1 page.*

Moriishi, K. et al., Critical role of PA28gamma in hepatitis C virus-associated steatogenesis and hepatocarcinogenesis, Proceedings of the National Academy of Sciences, 2007, vol. 104, No. 5, pp. 1661-1666.

Mori, Y. et al., Hepatitis C virus core protein: its coordinate roles with PA28gamma in metabolic abnormality and carcinogenicity in the liver, International Journal of Biochemistry and Cell Biology, 2008, vol. 40, No. 8, pp. 1437-1442.

Supplementary European Search Report dated Sep. 19, 2012, from the European Patent Office in corresponding European Application No. 09810032.4.

Wilk, S. et al., Properties of the Nuclear Proteasome Activator PA28r (REGr), Archives of Biochemistry and Biophysics, vol. 383, No. 2, pp. 265-271, 2000.

Moriya, K. et al., The core protein of hepatitis C virus induces hepatocellular carcinoma in transgenic mice, Nature Medicine 4, 1065-1067(1998).

Otsuka, M. et al., Hepatitis C Virus Core Protein Enhances p53 Function through Augmentation of DNA Binding Affinity and Transcriptional Ability, J. Biol. Chem., 275: 34122-34130(2000).

You, L.-R. et al., Hepatitis C Virus Core Protein Interacts with Cellular Putative RNA Helicase, J. Virol., 73:2841-2853 (1999).

Moriishi, K.et al., Proteasome Activator PA28r-Dependent Nuclear Retention and Degradation of Hepatitis C Virus Core Protein, J. Virol., 77, 19, 10237-10249(2003).

Yoshida, T. et al., Activation of STAT3 by the Hepatitis C Virus Core Protein Leads to Cellular Transformation, J. Exp. Med., 196:641-653(2002).

Moriishi, K. et al., Role of Proteasome-Activating Protein PA28gamma in Hepatis C Viral Infection, The 56th Annual Meeting of the Japanese Society for Virology, Okayama City, Japan, Oct. 26-28, 2008, Abstract No. 1E03.

Moriishi, K. et al., Proteasome activator PA28gamma is required for efficient growth of hepatitis c virus, 15th Int'l Symposium on Hepatitis C virus and Related Viruses, San Antonio, TX Oct. 5-9, 2008, p. 235.

International Search Report for PCT/JP2009/065072, dated Oct. 20, 2009.

* cited by examiner

*Primary Examiner* — Tracy Vivlemore
(74) *Attorney, Agent, or Firm* — Roylance, Abrams, Berdo & Goodman, L.L.P.

(57) ABSTRACT

The present invention provides an anti-hepatitis C virus composition that includes a substance that suppresses the expression or function of a PA28γ gene, a method for preventing hepatitis C viral infection or suppressing hepatitis C virus growth that includes the step of administering the composition to a subject, and a method for screening an effective component of an anti-hepatitis C virus composition that includes the step of selecting a substance that inhibits the expression or function of a PA28γ gene.

2 Claims, 4 Drawing Sheets

SEQUENCE LISTING

```
<160> NUMBER OF SEQ ID NOS: 6

<210> SEQ ID NO 1
<211> LENGTH: 21
<212> TYPE: DNA
<213> ORGANISM: Homo sapiens

<400> SEQUENCE: 1
aagtgaagct caaggttgat t                                              21

<210> SEQ ID NO 2
<211> LENGTH: 21
<212> TYPE: DNA
<213> ORGANISM: Homo sapiens
```

-continued

```
<400> SEQUENCE: 2
aaggttggat gagtgtgaag a                                               21

<210> SEQ ID NO 3
<211> LENGTH: 21
<212> TYPE: DNA
<213> ORGANISM: Homo sapiens

<400> SEQUENCE: 3
aagtgaggca gaagacttgg t                                               21

<210> SEQ ID NO 4
<211> LENGTH: 21
<212> TYPE: DNA
<213> ORGANISM: Homo sapiens

<400> SEQUENCE: 4
aaggtggatc aggaagtgaa g                                               21

<210> SEQ ID NO 5
<211> LENGTH: 765
<212> TYPE: DNA
<213> ORGANISM: Homo sapiens

<400> SEQUENCE: 5
atggcctcgt tgctgaaggt ggatcaggaa gtgaagctca aggttgattc tttcagggag     60
cggatcacaa gtgaggcaga agacttggtg gcaaattttt tcccaaagaa gttattagaa    120
cttgatagtt ttctgaagga accaatctta aacatccatg acctaactca gatccactct    180
gacatgaatc tcccagtccc tgaccccatt cttctcacca atagccatga tggactggat    240
ggtcccactt ataagaagcg aaggttggat gagtgtgaag aagccttcca aggaaccaag    300
gtgtttgtga tgcccaatgg gatgctgaaa agcaaccagc agctggtgga cattattgag    360
aaagtgaaac ctgagatccg gctgttgatt gagaaatgta cacggtcaa aatgtgggta    420 cagctcctga ttcccaggat agaagatgga aacaactttg gggtgtccat tcaggaggaa    480
acagttgcag agctaagaac tgttgagagt gaagctgcat cttatctgga ccagatttct    540
agatattata ttacaagagc caaattggtt tctaaaatag ctaaatatcc ccatgtggag    600
gactatcgcc gcaccgtgac agagattgat gagaaagaat atatcagcct tcggctcatc    660
atatcagagc tgaggaatca atatgtcact ctacatgaca tgatcctgaa aaatatcgag    720
aagatcaaac ggccccggag cagcaatgca gagactctgt actga                   765

<210> SEQ ID NO 6
<211> LENGTH: 69
<212> TYPE: DNA
<213> ORGANISM: Artificial Sequence
<220> FEATURE:
<223> OTHER INFORMATION: chemically synthesized shRNA-coding DNA

<400> SEQUENCE: 6
ggatccggtg gatcaggaag tgaagttcaa gagacttcac ttcctgatcc acctttttg     60 gaaaagctt                                                            69
```

ANTI-HEPATITIS C VIRUS COMPOSITION

TECHNICAL FIELD

The present invention mainly relates to pharmaceutical compositions useful for the prevention of hepatitis C virus (hereinafter, also referred to as "HCV") infection, or for the suppression of HCV growth.

BACKGROUND ART

Hepatitis C virus (HCV) has plus single-stranded RNA genome. The gigantic precursor protein of about 3,000 amino acids translated from the HCV RNA is cut into a virus particle-forming core protein and envelope protein, and other non-structural proteins by host cell-and virus-derived protein degrading enzymes.

The core protein is known to travel into the host cell nucleus, in addition to forming the virus particle. Recently, a strong involvement of the core protein in the onset of liver cancer in which the core protein modulates host cell functions in a variety of ways has been reported. Non-Patent Literature 1 describes, for example, HCV core protein-expressing transgenic mice developing liver cancer via fatty liver with high probability. In an effort to elucidate the molecular mechanism underlying the onset of liver cancer caused by the core protein, it has been common to identify host proteins that interact with the core protein, and analyze the functions of such proteins.

Many host proteins that interact with the core protein have been reported, including p53 (Non-Patent Literature 2), RNA helicase (Non-Patent Literature 3), STAT3 (Non-Patent Literature 4), and PA28γ (Non-Patent Literature 5).

Non-Patent Literature 5 reports that the core protein interacts with PA28γ, and localizes in the nucleus. Of note, PA28γ is known as a proteasome regulatory protein localized within the cell nucleus that interacts with 20S proteasome and improves the peptidase activity thereof. This literature also reports that the 44 to 71 amino acid region of the core protein is involved in both PA28γ binding and localization in the nucleus, and that the core protein is subject to PA28γ-dependent degradation. However, the specific mechanism underlying the involvement of the core protein in the onset of liver cancer is not fully elucidated in any of the foregoing literatures.

Patent Literature 1 discloses a screening method of a drug useful for the prevention and/or treatment of hepatitis C virus-associated disease, the method including the step of evaluating the inhibitory activity on the protein interaction between the hepatitis C virus core protein and PA28γ, and a preventive and/or therapeutic drug for hepatitis C virus-associated disease obtained by the method. However, this literature is concerned with suppressing the PA28γ-induced onset of a disease arising from the hepatitis C virus-derived core protein, specifically suppressing the progression of hepatitis conditions to fatty liver, cirrhosis, and liver cancer, and does not clarify functions that prevent hepatitis C virus infection, or suppress HCV growth. Thus, unlike antiviral drugs, the hepatitis C virus-associated disease preventive and/or therapeutic drug of this literature is not intended to suppress or reduce virus amounts, and only alleviates symptoms. Therefore, continuous administration is used, and clinical development is expected to take a long time because the persistent infection takes 10 to 15 years before developing into hepatitis C virus-associated diseases such as cirrhosis and liver cancer.

It would, however, be possible to cure HCV infections if the HCV could be cleared with the use of antiviral drugs. Considering that the current mainstream antiviral drugs target virus replication, it is considered possible to further improve anti-viral effects with an antiviral drug that uses a new mechanism to prevent viral infection or suppress virus growth.

CITATION LIST

Patent Literature

PTL: WO2008/041665

Non-Patent Literature

NPL 1: Nature Medicine 4, 1065-1067 (1998)
NPL 2: J. Biol. Chem., 275:34122-34130 (2000)
NPL 3: J. Virol., 73:2841-2853 (1999)
NPL 4: J. Exp. Med., 196:641-653 (2002)
NPL 5: J. Virol., 77, 19, 10237-10249 (2003)

SUMMARY OF INVENTION

Technical Problem

It is a primary object of the present invention to provide a composition useful for the prevention of HCV infection or suppression of HCV growth, a method for preventing HCV infection or suppressing HCV growth with the use of the composition, and a method for efficiently selecting a substance useful as an effective component of the composition.

Solution to Problem

The present inventors conducted extensive studies to achieve the foregoing object, and found the involvement of PA28γ in HCV infection. The invention has been completed based on this finding and upon further studies.

Specifically, the present invention concerns the following.

Item 1: An anti-hepatitis C virus composition comprising a substance that suppresses the expression or function of a PA28γ gene.

Item 2: A composition according to Item 1, wherein the substance that suppresses the expression or function of the PA28γ gene is any one of the following (a) to (c):

(a) a nucleic acid that suppresses the expression or function of the PA28γ gene;

(b) a modified nucleic acid that is a modification of the nucleic acid of (a); and (c) an expression vector capable of expressing the nucleic acid of (a).

Item 3: A composition according to Item 2, wherein the nucleic acid of (a) is an RNA.

Item 4: A composition according to Item 3, wherein the RNA is a siRNA (small interfering RNA) or a shRNA (short hairpin RNA).

Item 5: A composition according to any one of Items 1 to 4, wherein the composition is for preventing hepatitis C viral infection or for suppressing hepatitis C virus growth.

Specifically, a composition that contains, as an effective component, a substance that suppresses the expression or function of the PA28γ gene in order to prevent hepatitis C viral infection or suppress hepatitis C virus growth. Alternatively, a use of a PA28γ gene expression- or PA28γ gene function-suppressing substance for the manufacture of a medicament for preventing hepatitis C viral infection or suppressing hepatitis C virus growth.

Item 6: A method for preventing hepatitis C viral infection or suppressing hepatitis C virus growth, the method comprising the step of administering the composition of any one of Items 1 to 5 to a subject. Alternatively, a use of a PA28γ gene expression- or PA28γ gene function-suppressing substance in a method for preventing hepatitis C viral infection or suppressing hepatitis C virus growth.

Item 7: A method for screening an effective component of an anti-hepatitis C virus composition, the method comprising the steps of:
contacting a PA28γ gene-expressing cell or a cell capable of expressing the PA28γ gene with a test substance;
comparing a PA28γ gene expression level between the test substance-contacted cell and a control cell; and
selecting a test substance evaluated by the comparison to inhibit the expression of the PA28γ gene.

Specifically, a method for screening an effective component of an anti-hepatitis C virus composition, the method comprising the steps of:
contacting a PA28γ gene-expressing cell or to a cell capable of expressing the PA28γ gene with a test substance;
comparing a PA28γ gene expression level between the test substance-contacted cell and a control cell; and
selecting a test substance that lowers the PA28γ gene expression level compared to that of the control cell.

Item 8: A method for screening an effective component of an anti-hepatitis C virus composition, the method comprising the steps of:
administering a test substance to a reaction system that includes PA28γ, a trypsin-like substrate, and 20S proteasome;
comparing the test substance-administered system with a control with regard to the trypsin-like activity of the proteasome; and
selecting a test substance that suppresses the trypsin-like activity to a greater extent compared to the control.

The present invention is described below in detail.

As used herein, "anti-HCV" means the effect of inhibiting at least one of the steps in the HCV life cycle, which includes adsorption to a cell surface, invasion into the cell, uncoating, translation, replication, aggregation, transport into the cell membrane, and release from the cell. Further, "prevention of HCV infection or suppression of HCV growth" means protection from and/or suppression of HCV cell infection and HCV growth by the foregoing effect. For example, the prevention of HCV infection or suppression of HCV growth by the present invention include suppressing virus growth to suppress or reduce virus amounts, and to thereby prevent and/or suppress persistent HCV infection.

Specifically, the anti-HCV effect includes any of the following effects: inhibition of virus invasion into the cell, inhibition of uncoating, inhibition of virus particle aggregation, inhibition of transport into the cell membrane, and inhibition of virus particle release from the cell.

PA28γ is a known nuclear localized protein, also known as a proteasome regulatory protein. The amino acid sequence of PA28γ, and the coding base sequence of the protein are known. For example, human-derived PA28γ of the amino acid sequence represented by Swiss-Prot accession number P61289 is known. PA28γ also has non-human homologs, for example, in monkeys, mice, and pigs. The amino acid sequences of these proteins are available from Swiss-Prot, and all of these PA28γ proteins can be used in the present invention. The PA28γ described in the present invention is not limited to the wild-type proteins of the foregoing sequences, and, for example, may be a mutated protein of a sequence obtained by deletion or substitution of some of the amino acids of the wild-type protein, or by addition of other amino acid sequences. For example, the mutated protein may be a protein that has at least proteasome regulating activity or intranuclear transfer activity.

1. Anti-HCV Composition

An anti-HCV composition of the present invention comprises, as an effective component, a substance that suppresses the expression or function of the PA28γ gene.

As used herein, "expression" means protein production and localization of the protein in a functional state at the site of action. Accordingly, the "substance that suppresses expression" may be that which exhibits effects and suppresses expression at any stage of the process, including gene transcription, post-transcription modulation, translation into protein, post-translation modification, localization, intranuclear transfer, and protein folding.

Further, the term "function" means the effect exhibited by the actions of PA28γ. Thus, the "substance that suppresses function" means a substance that suppresses the actions of PA28γ. One of the actions of PA28γ is, for example, the activation of the trypsin-like activity of 20S proteasome. Thus, the "substance that suppresses function" includes compounds that inhibit the PA28γ-induced trypsin-like activity of 20S proteasome.

Specific examples of substances that suppress the expression or function of the gene include transcription inhibitory factors, RNA polymerase inhibitors, protein synthesis inhibitors, protein degrading enzymes, protein modifying factors, factors capable of inhibiting mRNA splicing or mRNA transfer into the cytoplasm, mRNA degrading factors, and factors that inactivate mRNA by binding thereto. Of these, substances that specifically act on the target molecule are preferred, so that adverse effects on other genes and proteins do not occur.

Examples of substances that specifically act on the target molecule include nucleic acids, antibodies, and peptides.

Antibodies include, for example, antibodies that have the effect of inhibiting the binding of PA28γ to proteasome. For specific effects, monoclonal antibodies are preferred.

Examples of peptides include peptides that have the effect of inhibiting the binding of PA28γ to proteasome. The peptides may be of solely a peptide structure, or may be composite peptides bound to sugar chains or fatty acids. Further, the peptides may be those in which a part of the amino acid residue side chain is modified, or protected by a protecting group.

Nucleic acids are particularly preferred in the present invention.

Nucleic acids may be DNA or RNA. RNA may be double-stranded RNA (dsRNA), single-stranded RNA (shRNA), or RNA of a double-stranded structure with single-strand overhangs.

Specific examples of nucleic acids that suppress the expression or function of the gene include ribozymes, antisense nucleic acids, aptamers, decoy nucleic acids, and small RNAs.

Examples of small RNAs include small interfering RNAs (siRNAs), microRNAs (miRNAs), small hairpin RNAs (shRNAs), and DsiRNAs (Dicer Substrate Small Interfering RNAs).

The following specifically describes siRNA or shRNA that causes mRNA degradation by RNA interference. Note, however, that the following descriptions are not intended to limit the present invention.

siRNA is a double-stranded oligo RNA with an RNA sequence and its complementary strand, the RNA sequence being homologous to the nucleotide sequence, or to a partial sequence thereof, of a target gene mRNA or an early transcript. shRNA (small hairpin RNA: shRNA) is a single-stranded RNA in which a sequence (first sequence) homologous to the target nucleotide sequence attaches to its complementary sequence (second sequence) via a hairpin loop portion, forming a double-stranded hairpin loop structure of the first and second sequences.

The length of the siRNA or shRNA sequence in a portion homologous to the target nucleotide sequence is not particularly limited, as long as it can cause RNA interference.

The full length of the siRNA or shRNA is also not limited as long as it can cause RNA interference, and is generally about 20 to 25, particularly about 21 to 23 bases pairs long.

Note that the full length of the shRNA refers to the length of the double-stranded portion of the shRNA double-stranded structure.

It is preferable that the sequence of the siRNA or shRNA homologous to the target nucleotide sequence has a sequence identity of 90% or more, preferably 95% or more, further preferably 98% or 99% or more with respect to the target nucleotide sequence.

The siRNA or shRNA at the 5'- or 3'-end may have an additional base that does not form a base pair. Though the additional base may be of DNA or RNA, siRNA stability can improve when the additional base is of DNA.

The length of the loop portion of the shRNA hairpin loop is not particularly limited, as long as it can cause RNA interference, and is generally about 3 to 23 bases, particularly about 6 to 9 bases. The nucleotide sequence of the loop portion is not particularly limited, as long as it can form a loop and allows the shRNA to cause RNA interference.

The siRNA and shRNA may be chemically synthesized using known methods, or may be synthesized in vitro with a transcription system that uses a promoter and RNA polymerase.

Chemical synthesis may be performed by synthesizing RNAs that have forward and reverse complementary sequences, and by binding these sequences at the self complementary portion. The synthesis using a promoter and RNA polymerase may be performed by synthesizing a template DNA of a structure in which the sense strand and antisense strand are joined at a loop downstream of a single promoter, and by transcribing the DNA into an RNA using RNA polymerase.

Specific examples of siRNA and shRNA include any of the sequences selected from positions 338 to 401 of the PA28γ mRNA of GenBank: XM_032767. Note that these examples should not be construed to limit the present invention.

The suppression of PA28γ gene expression by these RNAs may be transient or constant.

The nucleic acid may be modified. Modification may be performed at any portion of the nucleic acid molecule, as long as the nucleic acid can specifically bind to the target, and remains resistant to enzymatic degradation.

For example, the siRNA may be modified at least one of a nucleotide base (purine or pyrimidine), ribose, and phosphate.

Further, the nucleic acid may be contained in the form of an expression vector, so that it can stably reach the cell. The expression vector may be, for example, a plasmid vector, or a virus vector.

The composition of the present invention may contain a pharmaceutically acceptable carrier, in addition to the substance that suppresses the expression or function of the PA28γ gene.

The composition of the present invention may also contain, for example, anti-HCV effective components, such as interferon, pegylated interferon, and ribavirin, that work under different mechanisms from that of the present invention, and other effective components and known pharmaceutically acceptable additives, as long as the object of the present invention can be achieved.

The composition of the present invention can be used as an anti-HCV drug or anti-HCV agent by being formed into a preparation using known methods.

The dosage form of the anti-HCV drug or anti-HCV agent is not particularly limited, and may be appropriately selected depending on intended use. For example, the anti-HCV drug or anti-HCV agent may be used as a liquid or solid agent. For example, the liquid agent may be a liquid agent in which an effective amount of the substance that suppresses the expression or function of the PA28γ gene is dissolved, dispersed, or emulsified in water, or in a diluted solution or dispersion medium such as physiological saline. Examples of solid agents include capsule formulations, sachet agents, and tablets that include, either in solid form or as granules, an effective amount of the substance that suppresses the expression or function of the PA28γ gene.

Preferably, the anti-HCV drug or anti-HCV agent is designed based on a DDS (Drug Delivery System), so that the substance that suppresses the expression or function of the PA28γ gene can stably reach the liver or cells in the vicinity of the liver. For example, for the delivery of siRNA to the liver or to cells in the vicinity of the liver, cholesterol or derivatives thereof may be attached to the 5'-end and/or 3'-end of the siRNA molecule.

The composition of the present invention is particularly useful as a medicament or a drug for preventing HCV infection or suppressing HCV growth.

For example, the composition of the present invention can be suitably used for pre-infection administration, or for administration in the early stages of infection.

Further, the composition of the present invention can be used as a medicament for preventing infection in uninfected individuals.

Further, the composition of the present invention can be used as a medicament for suppressing HCV growth or for HCV clearance in, for example, individuals immediately after HCV infection, HCV infected individuals during its incubation period, or individuals infected with HCV but not showing liver abnormality.

Further, the composition of the present invention can be used for, for example, individuals having the possibility of being infected, infected individuals having the need to inhibit or delay the development of infection, or individuals who have failed to respond to other anti-HCV treatments.

By preventing HCV infection or suppressing HCV growth through pre-infection administration or administration in the early stage of infection, it is possible to prevent onset of hepatitis C, or prevent transition into the hepatitis active phase, for example, abnormal liver functions as manifested by persistently high GPT values increased 2 to 3 fold.

2. Method of Preventing HCV Infection or Suppressing HCV growth

The anti-HCV composition of the present invention can prevent HCV infection or suppress HCV growth by being administered to a subject either on its own or in the form of a preparation.

The term "subject" is a concept that encompasses whole individuals, organs, tissues, or cells of humans and non-human animals under the possibility of HCV infection or HCV growth, and includes, for example, tested individuals, and experimental animals.

The cells may be isolated cells or cultured cells.

Examples of non-human animals include non-human mammals such as mice, rats, pigs, monkeys, and tree shrews.

The dose may be appropriately set according to factors such as the method of administration, symptoms, the type or size of the subject, and drug characteristics.

The method of administration may be appropriately set, and may be oral administration or parenteral administration. Non-limiting examples of parenteral administration include systemic administration through, for example, veins, arteries, muscles, the abdominal cavity, or airway, and local administration to the liver or to areas in the vicinity of the liver.

Specifically, when the substance that suppresses the expression or function of the PA28γ gene is a small RNA, administration can be made according to known methods of administering small RNA, particularly, methods that target the liver.

The present invention is particularly suited as a method intended for individuals having the possibility of infection, and for patients in the non-active phase of acute hepatitis or chronic hepatitis. The invention is also suited as a method of administering the composition before infection, or in the non-active phase of acute hepatitis or chronic hepatitis.

By performing the administration at these stages to suppress or reduce virus amounts, the invention can prevent HCV infection or suppress HCV growth, and thus provides a cure for HCV infection, or a treatment for clearing HCV.

3. Screening Method

The effective component of the anti-hepatitis C virus composition of the present invention can be selected using a screening method that uses the suppression of PA28γ gene expression or function as an index.

For example, the screening method may be a method that includes the steps of:

contacting a PA28γ gene-expressing cell or a cell capable of expressing the PA28γ gene with a test substance;

comparing the test substance-contacted cell and a control cell with regard to a PA28γ gene expression level; and selecting a test substance evaluated by the comparison to inhibit the PA28γ gene expression.

The test substance may be a known compound or a novel compound. Examples include nucleic acids, proteins, peptides, and organic low-molecular compounds, either synthetic or natural.

The origin of the PA28γ gene-expressing cell or of a cell having the expression capability is not particularly limited, and, for example, mouse cells and human cells can be used. Further, the cell may be a living cell collected from established cell lines or animal liver, or may be a gene-introduced cell or siRNA-introduced cell, provided that the cell is capable of expressing the PA28γ gene.

The method used to contact the cell with the test substance is not particularly limited, and may be performed according to known methods, for example, by adding the test substance to a cell culture.

The measurement of PA28γ gene expression level can also be performed according to known methods. For example, the measurement may be made using a measurement method in which the cDNA obtained from mRNA by reverse-transcription is amplified and quantified by RT-PCR, a method that directly quantifies mRNA using probes (northern blotting), or a method that analyzes expression levels with a DNA microarray carrying groups of marker genes.

The PA28γ gene expression level of the test substance-contacted cell is compared with that of a control cell treated by the same conditions except that it has not been contacted with the test substance, and the test substance is evaluated to inhibit PA28γ gene expression when the test substance-contacted cell has a lower PA28γ gene expression level than the control cell. The substance evaluated to inhibit PA28γ gene expression is then selected as a candidate substance of the effective component of the anti-HCV composition of the present invention.

Alternatively, the screening method may be a method that includes the steps of:

administering a test substance to a reaction system that includes PA28γ, a trypsin-like substrate, and 20S proteasome;

comparing the test substance-administered system with a control with regard to the trypsin-like activity of the proteasome; and selecting a test substance that suppresses the trypsin-like activity to a greater extent compared to the control.

The trypsin-like substrate may be a known substrate used for the measurement of trypsin-like activity. Examples include Bz-VGR-AMC (benzoyl-Val-Gly-Arg-7-amido-4-methylcoumarin), and Boc-LRR-AMC (tert-butoxycarbonyl-Leu-Arg-Arg-7-amido-4-methylcoumarin).

The test substance may be a known compound or a novel compound. Examples include nucleic acids, proteins, peptides, and organic low-molecular compounds, either synthetic or natural.

The reaction system may include other substances, such as a buffer, a standard substance, and a quantifying reagent.

The control may be a reaction system that has the same conditions as the test substance-administered system except that the test substance has not been administered, or a reaction system that has the same conditions as the test substance-administered system except that a reference substance for comparison is administered instead of the test substance.

The method of comparing the trypsin-like activity of the proteasome may be performed according to known methods, and is not particularly limited. For example, the comparison may be made by comparing the measured fluorescence levels following the degradation of a fluorescence-labeled trypsin-like substrate.

Further, the screening method may be performed using a commercially available kit. For example, using a commercially available 20S proteasome kit, in a system using a trypsin-like substrate as a substrate and adding PA28γ, and further adding a test substance, screeing may be performed by measuring and comparing the trypsin-like activity of the proteasome.

By the comparison of the test substance-administered system and the control with regard to the trypsin-like activity of the proteasome, the test substance that suppresses the trypsin-like activity to a greater extent compared to the control is evaluated to inhibit the PA28γ-induced trypsin-like activity of the proteasome. The substance is then selected as a candidate substance of the effective component of the anti-HCV composition of the present invention.

As described above, the screening method of the present invention can screen for a substance effective for the prevention of HCV infection or suppression of HCV growth in vitro or in a cell-free system, both efficiently and conveniently.

Advantageous Effects of Invention

The present invention provides a pharmaceutical composition and a method useful for the prevention of HCV infection or suppression of HCV growth.

The present invention can inhibit HCV infection or suppress or reduce HCV production, and can thus prevent HCV infection, and provide a cure for the infection, or a treatment for clearing HCV.

There has been a report of a hepatitis C virus-associated disease preventive and/or therapeutic drug that contains an effective component substance obtained by a screening method that includes the step of evaluating the inhibitory activity on the protein interaction between hepatitis C virus core protein and PA28γ (Patent Literature 1). However, this literature only concerns the prevention and/or treatment of at least one disease selected from fatty liver, cirrhosis, and liver cancer that involve hepatitis C, as described in paragraphs [0010] and [0011] and elsewhere in the literature.

The present invention, on the other hand, is intended to prevent HCV infection, and to provide a cure for HCV infection or clear HCV. Since the liver is an organ with multidimensional capabilities, symptoms often do not appear quickly after infection with HCV. However, by the time the symptoms of hepatitis C are evident, the disease is its advanced stage, and a complete cure is difficult. Further, the infection poses the risk of developing into a disease in the future. It is therefore important to give appropriate treatment before HCV infection or in the early stages of HCV infection.

The present invention can provide protection from and/or suppression of HCV infection and HCV growth, and can thus clear HCV, and provide a cure for HCV infection.

Further, because the substance that suppresses the expression or function of the PA28γ gene is used as the effective component in the present invention, the effects are specific, and there are fewer side effects.

Further, the present invention provides a method that enables efficient and easy screening of a substance useful for the prevention of HCV infection or suppression of HCV growth.

As described above, the present invention provides a technique useful for the prevention of HCV infection or suppression of HCV growth.

DESCRIPTION OF EMBODIMENTS

The present invention is described in more detail based on Examples and Comparative Examples. It should be noted, however, that the present invention is not limited to the following descriptions.

1. Establishment of PA28γ Knockdown Cells

A DNA fragment that encodes a short hairpin RNA for knocking down the human PA28γ gene by RNA interference was designed according to the following procedure.

The following four sequences were selected as the target sequences from the open reading frame of the PA28γ gene.

| | |
|---|---|
| AAGTGAAGCTCAAGGTTGATT | SEQ ID NO: 1 |
| AAGGTTGGATGAGTGTGAAGA | SEQ ID NO: 2 |
| AAGTGAGGCAGAAGACTTGGT | SEQ ID NO: 3 |
| AAGGTGGATCAGGAAGTGAAG | SEQ ID NO: 4 |

The sequence of SEQ ID NO: 4, which has a remarkable expression suppressing effect, was selected from these sequences. The sequence of SEQ ID NO: 4 corresponds to positions 16 to 36 of the PA28γ coding region represented by SEQ ID NO: 5.

A DNA fragment that encodes a short hairpin RNA of this sequence was designed using the Insert Design Tool for the pSilencer® Vectors (Ambion; http://www.ambion.com/jp/techlib/misc/psilencer_converter.html). The sequence of the designed fragment is represented by SEQ ID NO: 6 in the sequence listing.

The DNA fragment was incorporated between the BamHI and Hind III sites of a pSilencer 2.1 U6-hygro vector (Ambion; Austin, Tex.), and introduced by lipofection to Huh7 OK1 cells sensitive to the hepatitis C virus JFH1 strain. The cells were then cultured for 1 week in a 10% fetal bovine serum Dulbecco's modified Eagle's medium supplemented with 0.1 mg/mL hygromycin. The cells were cloned by limiting dilution, and two clones, named C5 and C7, with low PA28γ expression levels were selected by western blotting.

Note that the Huh7 OK1 cells were obtained according to the method described in J. Virol., 82: 3480-3489, 2008. Specifically, the HCV replicon cell 9-13 strain was treated with interferon α, and, after clearing the virus replicon RNA, the cells were cloned by limiting dilution. Cloned cells with good JFH1 infection efficiency were then selected.

Separately, a commercially available pSilencer 2.1-U6 hygro negative control vector (Ambion) having no complementarity to human PA28γ gene was treated by the same procedure to establish single clones that had the same PA28γ expression level as the parental strain (control cells; hereinafter, also referred to as "control shRNA").

The Huh7 Ok1 cells, the control cells, and the PA28γ knockdown cells C5 and C7 were lysed, and the lysate was subjected to SDS-polyacrylamide gel electrophoresis for the detection of PA28γ and β-actin by western blotting using anti-PA28γ antibody (Affiniti) and anti-actin antibody (Sigma Aldrich Japan).

Figure 1:
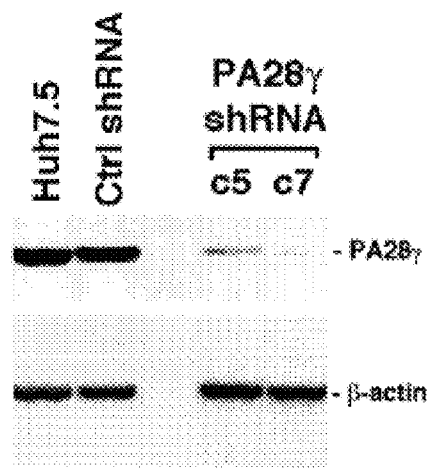
FIG. 1 represents the results of PA28γ and β-actin detection by western blotting in Hu7 Ok1 cells, control cells, and PA28γ knockdown cells C5 and C7.

The results are presented in FIG. 1

As presented in FIG. 1, the established cells C5 and C7 transfected with the shRNA against PA28γ had lower PA28γ expression levels than in the Huh7 Ok1 cells and in control cells (control shRNA).

2. Construction of RNA Interference-Resistant PA28γ Expression Plasmid

A PA28γ gene having the mutations G at position 18 to A, T at position 24 to C, and A at position 30 to G from positions 16 to 36 in the PA28γ coding region targeted by the shRNA of Section 1 above was incorporated in a plasmid pEF-FLAGGspGBK constructed based on Huang et al., Oncogene 14:405-414, 1997 to construct a PA28γ expression plasmid (pEFFLAGGsPA28gammaSI) resistant to shRNA.

3. Influence of PA28γ Constant Knockdown on HCV Infection

The control cells (control shRNA) and PA28γ knockdown cells C5 and C7 were transfected with pEFFLAGGspGBK or pEFFLAGGsPA28gammaSI plasmid. The next day, the medium was replaced with 10% fetal bovine serum Dulbecco's modified Eagle's medium supplemented with 3 μg/mL puromycin, and the cells were further cultured for 24 hours. The surviving cells were then inoculated in a 12-well plate ($2.5 \times 10^4$ cells/well), and infected with hepatitis C virus JFH1 at an MOI of 0.024.

Note that the JFH1 used was prepared according to the method described in Nature Protocols, 1 (5), 2334-2339, 2006.

The JFH1 gene-containing plasmid pJFH1 was cut with XbaI enzyme, blunted with Mung Bean nuclease, and virus RNA was synthesized using a MEGAscript T7 kit (Ambion). The virus RNA was transfected into Huh7 OK1 cells by electroporation under the conditions 260 V and 960 μF. A week later, Huh7OK1 was reinfected with the virus-containing cell supernatant, and the cell supernatant after 10 days was used as the virus fluid.

On the day after the infection, the medium was replaced with 10% fetal bovine serum Dulbecco's Eagle's medium, and the cells were cultured for 10 days. Using Huh7 OK1, the virus titer (ffu/mL) of the culture supernatant was measured according to the method of Wakita et al. (Nat. Med. 11:791-796, 2005), as follows. The Huh7 OK1 cells were infected with the culture supernatant to be measured at 37° C. for 3 hours. After being washed once with 10% FBS-DMEM, the cells were cultured for 96 hours with addition of 0.8% methylcellulose-containing 10% FBS-DMEM. The medium was removed, and the cells were fixed with addition of 100% methanol.

The rabbit anti-NS5A antibody prepared by immunizing the peptide from the amino acid residues 409 to 422 of NS5A according to the method described in J. Virol. 79:13473-13482, 2005 was allowed to react with Alexa Fluor® 488-anti-rabbit IgG antibody (Molecular Probe), and the fluorescent cell foci were counted to calculate the virus titer.

Figure 2:
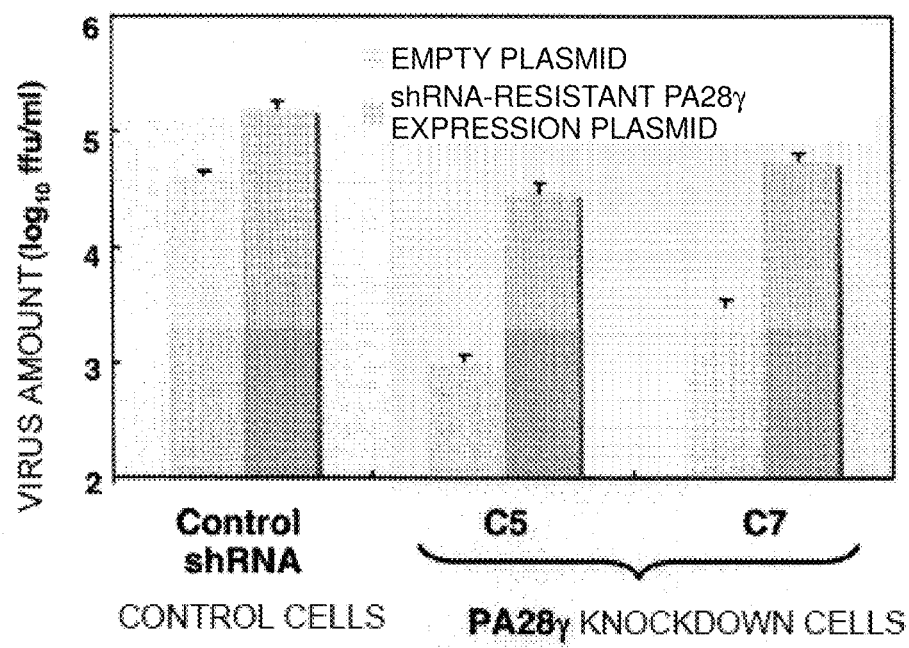
FIG. 2 represents the results of virus titer measurements of control cells (control shRNA) and PA28γ knockdown cells C5 and C7 after transfection with an empty plasmid (pEF-FLAGGspGBK) or a shRNA-resistant PA28γ expression plasmid (pEFFLAGGsPA28gammaSI).

The measurement results are presented in FIG. 2.

In FIG. 2, the values under the label "empty plasmid" are the results of viral infection after transfection with pEF-FLAGGspGBK plasmid (hereinafter, "empty plasmid").

The values under the label "shRNA-resistant PA28γ expression plasmid" are the results from viral infection after transfection with pEFFLAGGsPA28gammaSI plasmid (hereinafter, "RNA interference-resistant plasmid").

As shown in FIG. 2, virus production was significantly lower in PA28γ knockdown cells than in control cells when the cells were transfected with the empty plasmid.

Further, there was a slight increase in virus production in control cells transfected with the RNA interference-resistant plasmid than in empty plasmid-transfected control cells. On the other hand, in PA28γ knockdown cells C5 and C7 transfected with the RNA interference-resistant plasmid, virus production recovered to a level comparable to that in control cells transfected with the empty plasmid.

These results suggested that the reduction in virus production observed in the PA28γ knockdown cells was not due to a reduction in non-specific, non-PA28γ host proteins, but due to a reduction in PA28γ.

4. Influence of PA28γ Transient Knockdown on HCV Infection

A siRNA (Ambion, Cat No. 138669) that targets the sequence from positions 162 to 180 of the PA28γ gene coding region was mixed with 0.1 mL of Opti-MEM (Invitrogen). These were thoroughly mixed after addition of 1 μL of Lipofectamine™ RNAiMax (Invitrogen), and left to stand at room temperature for 20 min. Confluent Huh7 OK1 cells were detached with trypsin, and mixed in a 10% fetal bovine serum Dulbecco's modified Eagle's medium to make the concentration $10^5$ cells/mL. Then, 0.1 mL of the siRNA mixture prepared in advance was transferred to one of the wells in a 24-well plate, and 0.5 mL of the cell mixture was added thereto and thoroughly mixed.

After 24 hours, the cells were infected with JFH1 virus at MOI=0.03, and the amount of core protein and virus titer were measured 4 days later.

The amount of core protein and virus titer were also measured in the same manner in a negative control prepared by using Stealth™ RNAi Negative Control Low GC duplex (12935-200; Invitrogen).

The amount of core protein was measured for both the cells and the cell supernatant, using an Ortho HCV antigen ELISA test (Eiken Chemical Co., Ltd.). Virus titer was measured according to the method of Wakita et al. (Nat. Med. 11:791-796, 2005), as in Section 3 above.

The PA28γ expression levels were also measured by western blotting in cells transfected with the negative control siRNA, and in cells transfected with siRNA against PA28γ.

Figure 3:
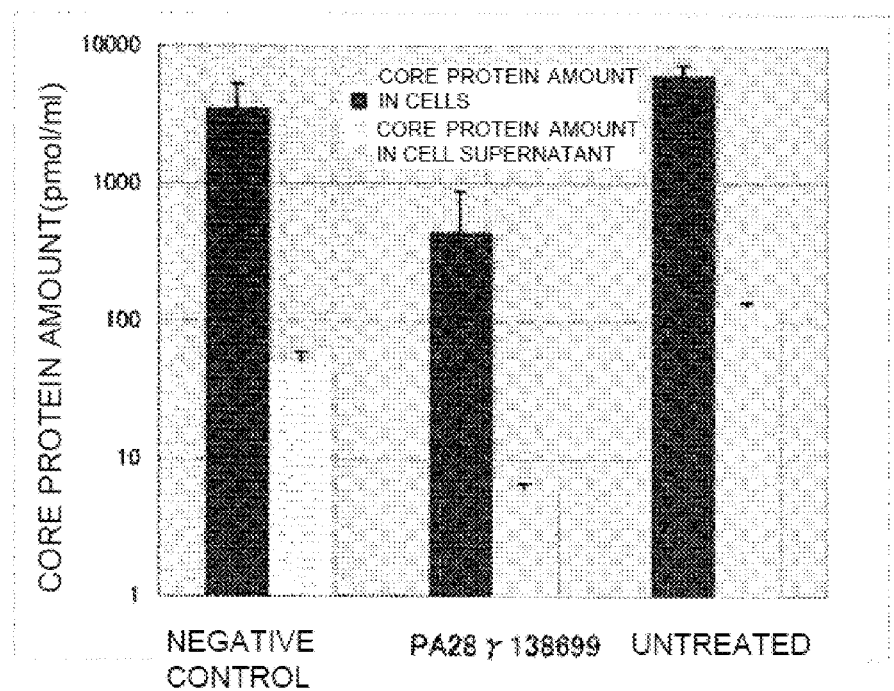
FIG. 3 represents the measurement results of the core protein amounts in virus infected cells and in the cell supernatant of the virus infected cells for a sample transfected with negative control siRNA (negative control), a sample transfected with siRNA against PA28γ (PA28γ138669), and a sample not transfected with siRNA (untreated).
Figure 4:
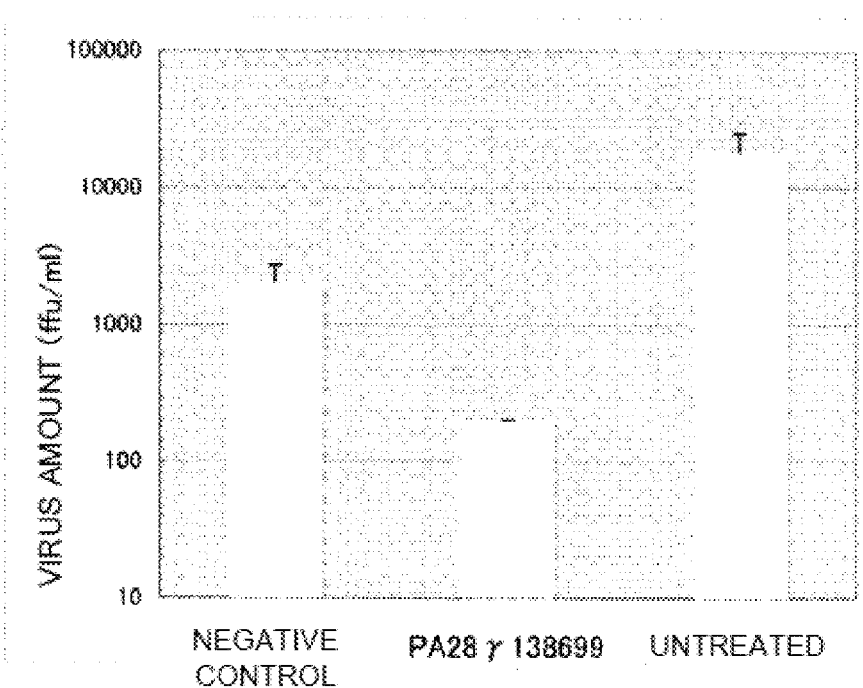
FIG. 4 represents the results of virus titer measurements for a sample transfected with negative control siRNA (negative control), a sample transfected with siRNA against PA28γ (PA28γ138669), and a sample not transfected with siRNA (untreated).
Figure 5:
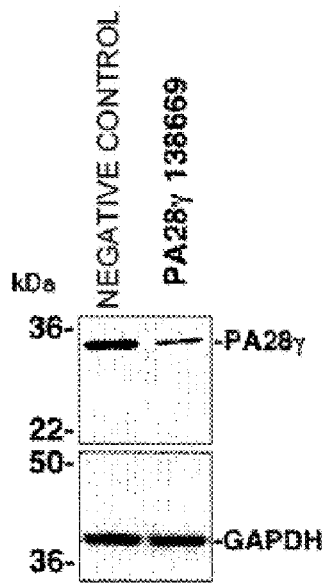
FIG. 5 represents the measurement results of PA28γ expression level by western blotting in cells transfected with negative control siRNA (negative control), and in cells transfected with siRNA against PA28γ (PA28γ138669).

The results are presented in FIGS. 3 to 5.

As shown in FIG. 3, the amounts of core protein in the cell supernatant and in the cells were lower in a sample (PA28γ138669) transfected with siRNA against PA28γ than in a sample (negative control) transfected with the negative control siRNA, and in a sample (untreated) not transfected with siRNA.

Further, as shown in FIG. 4, the virus amount was also smaller in PA28γ138669.

Further, as shown in FIG. 5, a western blotting analysis of the PA28γ levels in the cells revealed reduced PA28γ expression levels in PA28γ138669 than in the negative control, confirming the knockdown effect by siRNA.

The results thus confirmed that HCV virus growth could also be suppressed by the transient suppression of PA28γ expression by the introduction of siRNA that targets a different region of the PA28γ gene.

5. Influence of Replicon on Virus Replication

Virus replication by replicon was evaluated in the same manner except that the control cells and knockdown cells prepared in Section 1 above were used, as described in Krieger et al. (Krieger et al., J. Virol., 75:4614-4624, 2001).

A cDNA encoding Renilla luciferase was introduced between AscI and PmeI of a plasmid pFK-1389 neo/NS3-3'/NK5.1, instead of a neogene. The resulting plasmid pFK-1389 hRL/NS3-3/NK5.1 was cleaved at ScaI, and translated in vitro using a MEGAscript T7 kit (Ambion). A suspension of Huh7 cells (10×10⁶ cells/mL) was prepared, and 400 µl of the suspension was mixed with 10 µg of in vitro transcription RNA. This was followed by electroporation performed under the conditions 270 V and 960 µF using a Gene Pulser™ (Bio-Rad). The electroporated cells were suspended in 25-ml medium, and inoculated in a 12-well culture plate (1 ml/well). Then, luciferase activities at hour 4, 24, 48, and 96 post infection were measured using a Renilla Luciferase assay system (Promega).

The synthesized HCV replicon RNA, and the HCV replicon GND RNA with the inactivated RNA polymerase activity were transfected into control shRNA cells and PA28γ knockdown cells C5, and luciferase activity was measured.

The measured values in each combination were normalized by dividing the values after 24, 48, and 96 hours by the value after 4 hours.

Figure 6:
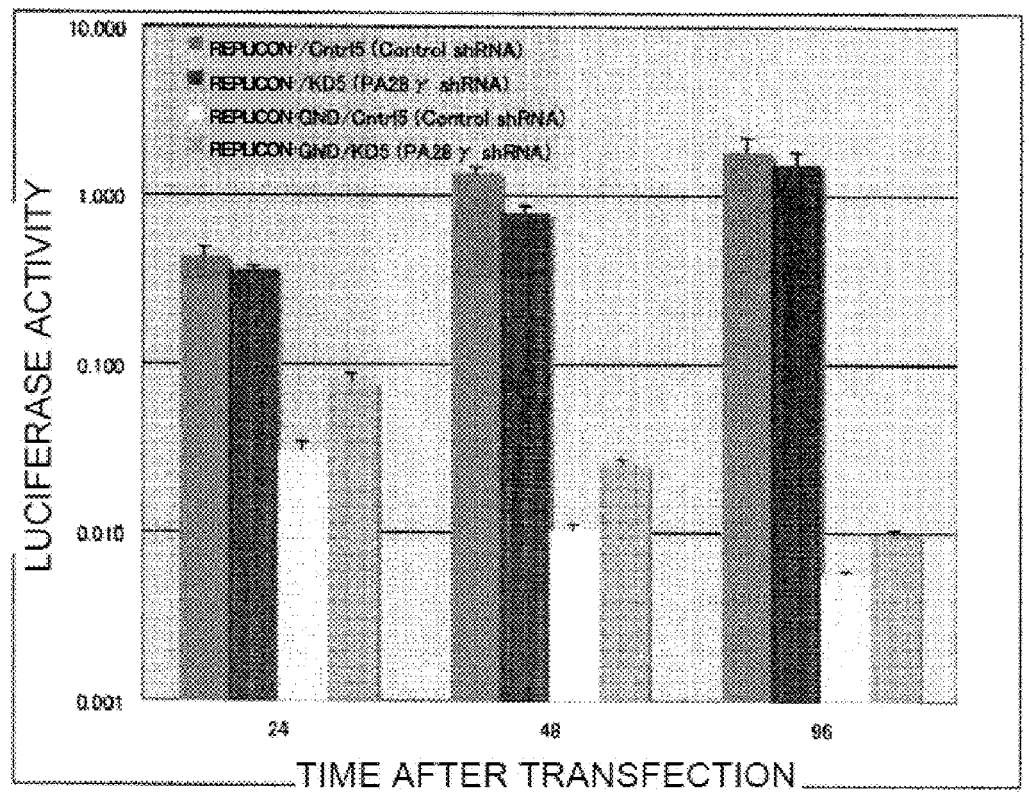
FIG. 6 represents the results of luciferase activity measurement conducted to examine the influence on virus replication, using control shRNA cells prepared by introducing HCV replicon RNA (replicon/Cntrl5), PA28γ knockdown cells C5 prepared by introducing HCV replicon RNA (replicon/KD5), PA28γ knockdown cells C5 prepared by introducing RNA polymerase activity-inactivated HCV replicon GND RNA (repliconGND/Cntrl5), and PA28γ knockdown cells C5 prepared by introducing RNA polymerase activity-inactivated HCV replicon GND RNA (repliconGND/KD5).

The results are presented in FIG. 6.

The luciferase values in the control cells (Cntrl5) and PA28γ knockdown cells (KD5) transfected with replicon RNA increased with time, showing replication. However, there was no difference in luciferase value between these cells. On the other hand, in the negative control cells transfected with replicon GND RNA, the luciferase values decreased with time, and the virus did not replicate.

The influence of PA28γ knockdown on virus replication was evaluated in this manner by observing virus replication after the introduction of replicon RNA. However, the influence of PA28γ knockdown on virus replication was not recognized. It is therefore considered that PA28γ inhibits viral infection or suppresses virus growth in any of the following stages: virus invasion, uncoating, virus particle aggregation, transport to the cell membrane, and release of virus particles.

6. Influence of PA28γ-Induced Trypsin-Like Proteasome Activity on HCV Infection

The Huh7 Ok1 cells described in Section 1 above were inoculated in a 24 well-plate (0.25×10⁵/well).

The cells in each well were then transfected with a pEF FLAG Gs pGKpuro plasmid having incorporated the PA28γ or PA28γ mutant gene, and with an empty plasmid (0.25 µg each), using Lipofectamine LTX and Plusreagent (Invitrogen).

G150S, N151Y, P245Y, or K188E was used as the PA28γ mutant. G150S is a mutant having a mutation at the amino acid residue 150 (Gly150Ser) of the PA28γ amino acid sequence. N151Y is a mutant having a mutation at the amino acid residue 151 (Asn151Tyr) of the PA28γ amino acid sequence. P245Y is a mutant having a mutation at the amino acid residue 245 (Pro245Tyr) of the PA28γ amino acid sequence. K188E is a mutant having a mutation at the amino acid residue 188 (Lys188Glu) of the PA28γ amino acid sequence. PA28γ activates the trypsin activity of 20S proteasome. However, G150S cannot activate 20S proteasome. N151Y cannot activate 20S proteasome. P245Y cannot bind to 20S proteasome. K188E activates the chymotrypsin activity of 20S proteasome, but cannot activate trypsin activity (Proc. Natl. Acad. Sci. USA, 95, 2807-2811, 1998).

Each cell after the transfection was infected with JFH1 virus at MOI=0.03.

Virus production at day 4 post infection was quantified by titration.

Figure 7:
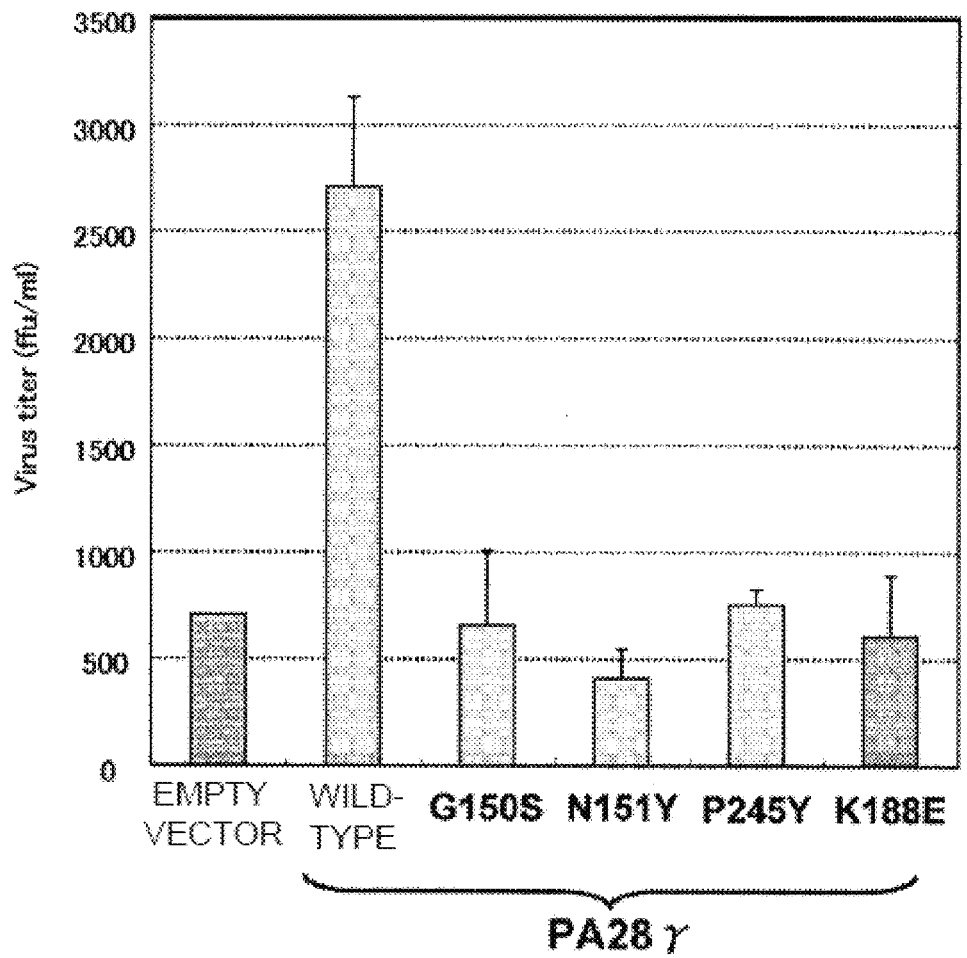
FIG. 7 represents the results of the virus production measurements using virus-infected PA28γ knockdown cells transfecting a PA28γ (native form), PA28γ mutant (G150S, N151Y, P245Y, or K188E) gene-incorporated plasmid, or an empty plasmid.

The results are presented in FIG. 7.

As shown in FIG. 7, virus production upon virus infection was higher when the plasmid having incorporated the PA28γ gene was transfected into the PA28γ knockdown cells than when the empty plasmid was transfected.

However, there was no increase in virus production when the plasmid transfected into the cells had incorporated the G150S, N151Y, or P245Y gene—a PA28γ mutant that cannot activate the proteasome. There was also no increase in virus production when the plasmid transfected into the cells had incorporated the K188E gene—a PA28γ mutant that cannot activate the trypsin-like activity of the proteasome but activates the chymotrypsin-like activity.

These results suggested that the PA28γ-induced activation of the trypsin-like activity of 20S proteasome is necessary for virus production.

Sequence Listing Free Text

SEQ ID NO: 1: An example of a PA28γ gene RNA interference target sequence

SEQ ID NO: 2: An example of a PA28γ gene RNA interference target sequence

SEQ ID NO: 3: An example of a PA28γ gene RNA interference target sequence

SEQ ID NO: 4: An example of a PA28γ gene RNA interference target sequence

SEQ ID NO: 5: PA28γ coding region

SEQ ID NO: 6: DNA fragment that encodes a short hairpin RNA against the sequence of SEQ ID NO:4

The invention claimed is:

1. A method for preventing hepatitis C viral infection or suppressing hepatitis C virus growth, the method comprising the step of administering a pharmaceutical composition comprising an effective amount of a compound that inhibits the PA28γ-induced activation of the trypsin-like activity of 20S proteasome to an animal in need thereof, wherein the compound is one or more of:

(a) a siRNA or a shRNA having binding specificity for at least one polynucleotide sequence selected from the group consisting of the polynucleotide sequence represented by SEQ ID NO:4 and the polynucleotide sequence from positions 162 to 180 of SEQ ID NO:5;
(b) a modified siRNA or a modified shRNA that is a modification of the siRNA or the shRNA of (a); and
(c) an expression vector capable of expressing the siRNA or the shRNA of (a) or the modified siRNA or the modified shRNA of (b).

2. The method of claim 1, wherein the siRNA or the shRNA of (a) is about 20-25 paired bases in length.

* * * * *

UNITED STATES PATENT AND TRADEMARK OFFICE
CERTIFICATE OF CORRECTION

PATENT NO.        : 8,580,759 B2
APPLICATION NO.   : 13/060474
DATED             : November 12, 2013
INVENTOR(S)       : Moriishi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 83 days.

Signed and Sealed this
Twenty-second Day of September, 2015

Michelle K. Lee
*Director of the United States Patent and Trademark Office*